US009964634B2

(12) United States Patent
Nikolov et al.

(10) Patent No.: US 9,964,634 B2
(45) Date of Patent: May 8, 2018

(54) IMAGING TISSUE MOTION ESTIMATION

(71) Applicant: B-K MEDICAL APS, Herlev (DK)

(72) Inventors: Svetoslav Ivanov Nikolov, Farum (DK); Jacob Kortbek, Odense (DK)

(73) Assignee: B-K Medical Aps, Herlev (DK)

( * ) Notice: Subject to any disclaimer, the term of this patent is extended or adjusted under 35 U.S.C. 154(b) by 515 days.

(21) Appl. No.: 14/429,639

(22) PCT Filed: Sep. 20, 2012

(86) PCT No.: PCT/IB2012/001854
§ 371 (c)(1),
(2) Date: Mar. 19, 2015

(87) PCT Pub. No.: WO2014/045074
PCT Pub. Date: Mar. 27, 2014

(65) Prior Publication Data
US 2015/0234040 A1    Aug. 20, 2015

(51) Int. Cl.
*G01S 7/52* (2006.01)
(52) U.S. Cl.
CPC .............................. *G01S 7/52017* (2013.01)
(58) Field of Classification Search
CPC ................................................ G01S 7/52017
See application file for complete search history.

(56) References Cited

U.S. PATENT DOCUMENTS

| 5,462,058 A | 10/1995 | Yamada et al. |
| 6,508,768 B1 | 1/2003 | Hall et al. |
| 2006/0052696 A1 | 3/2006 | Shiina et al. |

OTHER PUBLICATIONS

International Search Report for PCT/IB2012/001854, published as WO2014/045074, dated Jun. 6, 2013.
Alam, S. Kaisar and Ophir, Jonathan, The Effect of Nonlinear Signal Transformations on Bias Errors in Elastography, IEEE Transactions on Ultrasoncis, Ferroelectrics and Frequency Control, vol. 47, No. 1, Jan. 2000.
Cespedes, Ignacio and Ophir, Jonathan, Reduction of Image Noise in Elastography, Ultrasonic Imaging 15, 89-102, 1993.
Hasegawa, Hideyuki and Kanai, Hiroshi, Reduction of Influence of Variation in Center Frequencies of RF Echoes on Estimation of Artery-Wall Strain, IEEE Transactions on Ultrasoncis, Ferroelectrics and Frequency Control, vol. 55, No. 9, Sep. 2008.
Loupas, Thanasis, Powers, J.T., and Gill, Robert W., An Axial Velocity Estimator for Ultrasound Blood Flow Imaging, Based on a Full Evaluation of the Doppler Equation by Means of a Two-Dimensional Autocorrelation Approach, IEEE Transactions on Ultrasoncis, Ferroelectrics and Frequency Control, vol. 42, No. 4, Jul. 1995.

(Continued)

*Primary Examiner* — Michael Rozanski
(74) *Attorney, Agent, or Firm* — Anthony M. Del Zoppo, III; Driggs, Hogg, Daugherty & Del Zoppo, Co., LPA

(57) ABSTRACT

A motion processor (118) includes a motion estimator (306) that iteratively estimates a motion between a pair of consecutive frames of pre-processed echoes, wherein the motion estimator (306) generates the estimated motion based on at least on one iteration. A method includes iteratively estimating tissue motion between a pair of consecutive frames of pre-processed echoes over at least one iteration.

20 Claims, 6 Drawing Sheets

(56) References Cited

OTHER PUBLICATIONS

Pesavento, Andreas, Perrey, Christian, Krueger, Martin and Ermert, Helmut, A Time-Efficient and Accurate Strain Estimation Concept for Ultrasonic Elastography Using Iterative Phase Zero Estimation, IEEE Transactions on Ultrasoncis, Ferroelectrics and Frequency Control, vol. 46, No. 5, Sep. 1999.

Zahiri-Azar, Reza, Goksel, Orcun, Yao, Ta Shan, Dehghan, Ehsan, Yan, Joseph and Salcudean, Septimiu E., Methods for the Estimation of Sub-sample Motion of Digitized Ultrasound Echo Signals in Two Dimensions, 30th Annual International IEEE EMBS Conference, Vancouver, BC, Canada, Aug. 20-24, 2008.

Jiang, Zhqiang and Liu, Paul, Modified Phase Zero Method for Ultrasound Freehand Strain Imaging.

IMAGING TISSUE MOTION ESTIMATION

RELATED APPLICATION

This application is a national filing of PCT application Serial No. PCT/IB2012/001854, filed Sep. 20, 2012, published as WO/2014/045074 on Mar. 27, 2014.

TECHNICAL FIELD

The following generally relates to imaging and more particularly to imaging tissue motion estimation and is described herein with particular attention to ultrasound imaging.

BACKGROUND

Imaging such as ultrasound (US) imaging has provided useful information about the interior characteristics of a subject under examination. Tissue motion estimation has been used in connection with imaging such as elastography, which has also been referred to as strain imaging, strain rate imaging, and elasticity imaging. With such imaging, stiffness or strain images of soft tissue are used to detect or classify unhealthy tissue (such as a tumor, necrotic tissue, etc.) that is stiffer relative to surrounding healthy or normal soft tissue. For this, a mechanical compression or vibration is applied to a region of interest, and the unhealthy tissue compresses less than the surrounding tissue since the strain is less than the surrounding tissue.

With axial motion (motion along the direction of the ultrasound beam), block matching, phase-shift, and frequency estimation have been used to estimate motion. Time-shift techniques, also known as speckle tracking, have used block-matching. Data used in speckle tracking can be envelope detected data (no phase information) or radio-frequency (RF) data. The RF data is data that comes before envelope-detection. For this, a one dimensional (1D) or two dimensional (2D) set of data (kernel) is chosen from a first frame. This kernel is compared to data sets of same size from a next frame within a pre-defined search region. When a best match is found, the displacement is estimated from the difference in the locations of the two regions.

Different matching algorithms have been used with block-matching. Examples of the matching algorithms have included sum of absolute differences, sum of squared differences, and maximum cross-correlation. Unfortunately, these techniques require high sampling frequency, for example, eight times the carrier frequency, which is four times the Nyquist requirement. Furthermore, the sum of absolute differences approach and the sum of squared differences approach are susceptible to identifying false minimums, and the maximum cross-correlation approach is susceptible to identifying false peaks, especially when the cross-correlation is performed on RF data.

Elastography has also required sub-sample precision of the estimates. For this, a polynomial approximation is fitted to the maximum cross-correlation or sum of absolute differences functions. One implementation of cross correlation is fastest if whole matrixes are multiplied, and the result (which is also a matrix) is compared to a temporary matrix. Adding interpolation to the cross-correlation means that the results for the different lags must be kept in memory, which increases the need for RAM. Memory access is often the bottleneck of modern systems. Using block-matching for high-precision displacement estimation requires the transfer of large amounts of data.

The phase shift estimation works exclusively with either RF data or complex-valued baseband signals, known also as in-phase and quadrature-phase signals. The fundament for phase-shift displacement estimation is the assumption that the measured signals are narrow-band and can be described as $x(t)=a(t) \exp(-j\omega t)$, where $\omega$ is angular frequency, to $\omega=2\pi f$. The frequency of the ultrasound signal is f, and is often the carrier frequency of the pulse sent in the tissue. The time t is measured from the start of the emission for the current line. The classical estimation procedure is to take samples from the same depth from frame 1 and frame 2. It is assumed that the only difference between the two frames is due to motion.

It is also assumed that the signal $x_2(t)$ from frame 2 is a time-shifted version of the signal $x_1(t)$ from frame 1, or $x_2(t)=x_1(t-t_m)$. If $t_m$ is positive then the motion is away from the transducer. Assuming a narrow-band model: $x_1(t)=a(t) \cdot \exp(-j\omega t)$ and $x_2(t)=a(t-t_m) \cdot \exp(-j\omega t+j\omega t_m)$. The lag-zero cross correlation between $x_1(t)$ and $x_2(t)$ can be estimated as: $R_{12}(0)=\int a(t) \exp(-j\omega t) \cdot a(t_m-t) \exp(j\omega t-j\omega t_m)$ dt. The result is: $R_{12}(0)=\exp(-j\omega_m) \cdot \int a(t) \cdot a(t_m-t)$. The envelope a(t) is typically a slowly varying function, and the time shift can be found from the phase of the complex correlation function $R_{12}(0)$: $\Phi_m = \angle(R_{12}(0))=-j\omega t_m$. The relation between depth and time is given by:

$$t = \frac{2z}{c},$$

where t is time, z is depth and c is speed of sound.

The displacement in depth u, which corresponds to the phase shift $\varphi_m$, is $$u = -\frac{c}{4\pi f}\phi_m.$$

The frequency has been chosen constant, but for high-precision estimates, it must reflect the instantaneous mean frequency of the signal at a given depth. In practice, the estimation of $R_{12}(0)$ is done by multiplying every sample from frame 1 inside the estimation kernel with every sample from frame 2 inside the estimation kernel, located at the same place within the frame. Then, the resulting products are added together. An arctangent is used to determine the phase shift. Unfortunately, the phase shift method is susceptible to aliasing. The phase wraps around $\pi$. So a robust phase unwrapping algorithm is needed.

Another issue with this method is that the variance of the estimates increases with motion. That is, low motion is detected reliably, while large motion is not reliably detected. Variants have included zero-phase search of $R_{12}$ and phase separation, where the phases of the IQ signals from the two frames are subtracted. These variants seek to overcome the aliasing problem and to decrease the variance. Their estimations start from the transducer surface, and then they keep track of the accumulated phase shift. However, if an error is made at one depth, the error may propagate to the end of the frame.

A combined autocorrelation approach estimates based on the combination of block matching and phase estimation. For both, the block matching and phase estimation, the cross-correlation function is estimated for every pixel where an estimate is needed. A correlation window from the first frame is matched against correlation windows at different displacements from the second frame. For every displacement (k, l) the normalized cross-correlation function is estimated. The maximum value of $R_{12}$(k, l) is kept.

The total displacement is found from the lag at which the cross-correlation is evaluated (k, l) and from the phase of the cross-correlation at that lag:

$$\phi = \angle(R_{12}(k, l)),$$

$$t_m = -\frac{\phi}{2\pi f} + \frac{k}{2f_s},$$

and $$u = -\frac{c}{2t_m},$$

where $f_s$ is the sampling frequency, and k is a sample in depth. This approach can be used to overcome the aliasing, as it is expected that $R_{12}$ will have a maximum at a sample k within the right multiple of periods. However, the detection of the right peak of $R_{12}$ requires wideband pulses, the reliable estimation of φ requires narrowband pulses, if a wrong peak is chosen, then the result shows up in the image, and this approach cannot take advantage of "envelope compression."

Elastography is particularly sensitive to the variance of motion estimates, as strain is the first derivative of the motion. The motion within the kernel (correlation window) is not uniform. The estimation procedure aims at estimating the motion of the center of the correlation window. If there is a strong scatter at the edges of the window, then it dominates motion estimation. A periodic variation is present in the motion estimates that gives rise to an artifact known as "zebra" artifact in strain imaging. To reduce the effect of the zebra artifact, the literature suggests compressing the envelope of the RF signal prior to the estimation. The compression function known from literature is: $x_c(t)$=sgn(x (t))×$\log_{10}$(1+cs×abs (x(t))), where sgn(x) returns the sign of the value and cs is a constant that controls the level of compression.

SUMMARY

Aspects of the application address the above matters, and others.

In one aspect, a motion processor (118) includes a motion estimator (306) that iteratively estimates a motion between a pair of consecutive frames of pre-processed echoes, wherein the motion estimator (306) generates the estimated motion based on at least on one iteration.

In another aspect, a method includes iteratively estimating tissue motion between a pair of consecutive frames of pre-processed echoes over at least one iteration In another aspect, a computer readable storage medium is encoded with computer executable instructions, which, when executed by a processor, causes the processor to: determine an initial motion estimate based on a pair of consecutive compressed frames of pre-processed echoes, a lag-zero cross correlation, and a mean frequency, determine non-zero cross-correlation lags based on the initial motion estimate, multiply, element-by-element, elements in the pairs of compressed consecutive frames of pre-processed echoes at the non-zero cross-correlation lags, producing a product matrix, convolve the product matrix with a 2D weighting function, remove discontinuities in phase estimation at borders, producing a de-glitched convolved matrix, determine a phase shift of the de-glitched convolved matrix, unwrap a phase of the de-glitched convolved matrix based on the determined phase shift, and convert the unwrapped phase to the motion estimate.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which.

DETAILED DESCRIPTION

Figure 1:
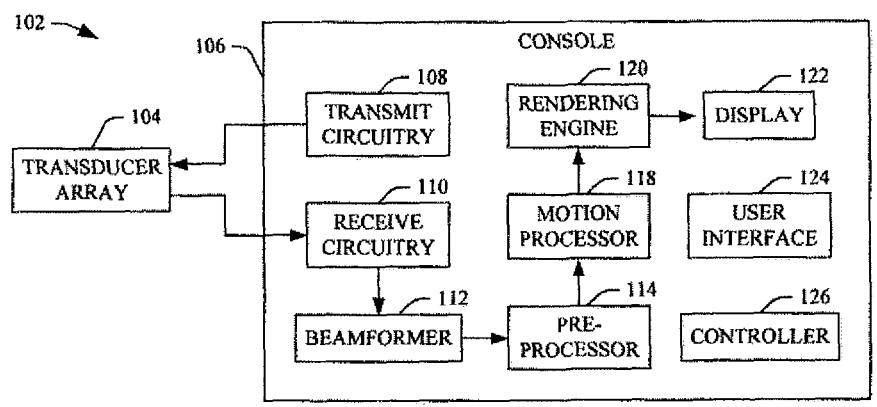
FIG. 1 schematically illustrates an example ultrasound imaging system with a motion processor.

FIG. 1 schematically illustrates an example imaging system 102 such as an ultrasound imaging system. The illustrated imaging system 102 includes a transducer array 104 interfaced with a console 106. The transducer array 104 includes a plurality of transducer elements (not visible) configured to transmit ultrasound signals into a field of view and receive echo signals generated in response to an interaction of the transmit ultrasound signals with tissue in the field of view. The transducer array 104 can be linear, curved, and/or otherwise shaped, fully populated, sparse and/or a combination thereof, one dimensional (1D) or two dimensional (2D), etc.

The console 106 includes transmit circuitry 108 that actuates the transducer elements to transmit the ultrasound signals. In one instance, this includes actuating the transducer elements to apply a different mechanical vibration to the tissue in the region of view for at least two frames for elastography applications. Receive circuitry 110 receives a set of echoes generated in response to the transmitted ultrasound signals. The echoes, generally, are a result of the interaction between the emitted ultrasound signals and the tissue (e.g., organ, tumor, etc.) in the scan field of view. For elastography, the echoes include tissue motion or displacement information between the frames of data. A beamformer 112 processes the received echoes, e.g., by applying time delays and weights to the echoes and summing the resulting echoes, producing an RF signal, or scan lines. A frame consisted of a set of scan lines that together form a 2D image of the field of view.

Figure 2:
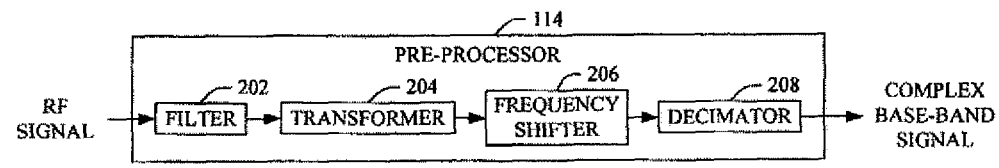
FIG. 2 schematically illustrates a pre-processor of the ultrasound imaging system.

The console 106 also includes a pre-processor 114 that pre-processes the RF signal. A non-limiting example of the pre-processor 114 is shown in FIG. 2. In this example, the pre-processor 114 includes a filter 202 that filters the RF signal, for example, via a band-pass sliding filter. Generally, such a filter maximizes the signal-to-noise ratio, and changes its characteristics as a function of depth, to match the properties of the RF signal. A transformer 204 applies a Hilbert or other transform, creating a complex signal from the real input. A frequency shifter 206 shifts the spectrum of the complex signal towards baseband (zero Hertz, or 0.0 Hz), for example, by mixing the complex signal with a predetermined mixing frequency. A decimator 208 decimates this signal (e.g., by a factor of 2 or more), preserving the data rate, without loss of information. The pre-processor 114 outputs a complex base-band signal.

Returning to FIG. 1, a motion processor 118 processes pairs of adjacent frames of the complex base-band signals. Such processing may include estimating tissue motion between the frames of data. As described in greater detail below, in one instance, the processing includes an iterative refinement of the motion estimates through phase-shift estimation using cross-correlation. Such an approach may lead to smooth motion maps (i.e., decreased variance of the tissue motion estimates), reduced noise artifacts, and/or increased contrast (i.e., detectability of structures) with elastography and/or other images, while achieving high precision with a reduced data set. Although the motion estimator 306 is shown as part of the console 106, it is to be appreciated that the motion estimator 306 may alternatively be remote from the console 106, for example, as part of a computer and/or other computing device.

A rendering engine 120 is configured to at least generate elastography or other images based on the processed frames. The elastography images can be visually presented via a display 122 and/or other display, stored, conveyed to another device, and/or otherwise utilized. A user interface (UI) 124 include one or more input devices (e.g., a mouse, keyboard, etc.), which allows for user interaction with the system 102. A controller 126 controls the various components of the imaging system 102. For example, such control may include actuating or exciting individual or groups of transducer elements of the transducer array 104 for an A-mode, B-mode, C-plane, and/or other data acquisition mode, steering and/or focusing the transmitted and/or received signal, etc.

The console 106 may include one or more processors (e.g., a central processing unit (CPU), graphics processing unit (GPU), etc.) that execute one or more computer readable instructions encoded or embedded on computer readable storage medium such as physical memory and other non-transitory medium. Additional or alternatively, the instructions can be carried in a signal, carrier wave and other transitory or non-computer readable storage medium. In one instance, executing the instructions, in connection with the one or more processors, implements one or more of the beamformer 112, the pre-processor 114, the motion estimator 306, the rendering engine 120, and/or other components of the imaging system 102.

Figure 3:
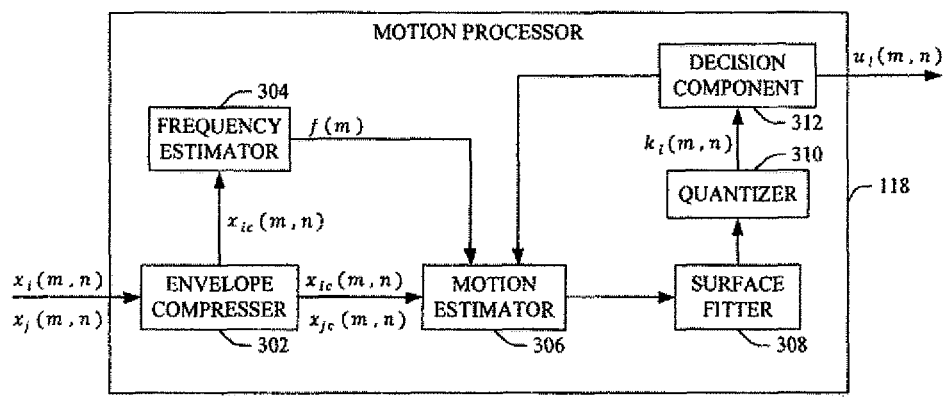
FIG. 3 schematically illustrates a motion estimator of the motion processor.

As briefly discussed above, the motion processor 118 processes pairs of adjacent frames of the complex base-band signals and estimates tissue motion between the frames using a iterative approach, FIG. 3 schematically illustrates an example of the motion processor 118.

An envelope compressor 302 receives, as input, two adjacent frames of the complex base-band signals $x_i(m, n)$ and $x_j(m, n)$, where i and j are frame indexes of adjacent frames (e.g., frames 1 and 2, frames 2 and 3, etc.), m is a sample index along a scan line, and n is a scan line index. $x_i(m, n)$ and $x_j(m, n)$ can be processed as matrices, where m is the matrix row index and n is the matrix column index, as vectors and/or as individual elements. The envelope compressor 302 compresses the envelope, while preserving the phase, producing $x_{ic}(m, n)$ and $x_{jc}(m, n)$, where c indicates compressed, which may facilitate reducing "zebra" artifacts.

By way of non-limiting example, the input signal is formed of complex samples: $x=x_r+jx_i$, where $x_r$ is the real (in-phase) component and $x_i$ is the imaginary (quadrature-phase) component. The compressed signals are found as: $x_c=x_{cr}+jx_{ci}$, $$x_{cr} = \frac{x_r}{|x|} \cdot \sqrt{\sqrt{|x|}},$$

and $$x_{ir} = \frac{x_i}{|x|} \cdot \sqrt{\sqrt{|x|}},$$

where |x| is the envelope (magnitude) of the signal, and can be found as $$|x| = 1 + \sqrt{x_r^2 + x_i^2}.$$

In one instance, a constant one (1) is added to prevent division by zero. The built-in instructions of the CPU and/or GPU can be used to compute the square root.

A frequency estimator 304 receives, as input, the compressed frame $x_{ic}(m, n)$ and estimates a mean frequency $f(m)$, e.g., for every depth, based thereon. The attenuation of ultrasound is frequency-dependent, hence the mean (center) frequency changes as a function of the depth. The resulting center frequency is a function of the center frequency of transmitted pulse, the impulse response of the transducer, the frequency-dependent attenuation, and the properties of the sliding filter. Scanners use different transmit pulses and sliding filters depending on the application. Furthermore the frequency dependent attenuation is a function of the tissue being scanned.

Generally, every time a new frame is input, a mean frequency $f(m)$ is estimated to match the scanned tissue and system setup. The input is the complex signal discrete $x_{ic}(m, n)$, which represents a matrix, where the index m is in axial direction (depth), and the index n is in lateral direction. The estimation of the frequency is done from the phase of the lag-1 complex autocorrelation function $$R_{ii}(m, n; 1, 0) = \sum_{v=-\frac{V}{2}}^{\frac{V}{2}} \sum_{w=-\frac{W}{2}}^{\frac{W}{2}} x_{ic}(m+v, n+w) \times x_{ic}^*(m+v+1, n+w),$$

where $R_{ii}(m, n; 1, 0)$ is the complex autocorrelation at pixel/position (m, n), and lag 1 in axial direction (along m) and lag 0 in lateral direction (along n).

An averaging window consists of V rows (samples) and W columns (lines), and the superscript •* denotes complex conjugation. The autocorrelation function is complex: $R_{ii}(m, n; 1,0) = R_{iir}(m, n; 1,0) + jR_{iii}(m, n; 1,0)$. The instantaneous frequency at pixel (m, n) is estimated as $$\phi(m, n) = \arctan \frac{R_{iii}(m, n; 1, 0)}{R_{iir}(m, n; 1, 0)}.$$

The phase is unwrapped using a standard or other unwrapping procedure (an example of which is described below in connection with FIG. 4): $\Phi$=unwrap($\Phi$), where $\Phi$ represents the whole matrix of phase estimates, and $$\hat{f}_i(m, n) = -\frac{\phi(m, n)}{2\pi} \cdot f_s + f_{mix}.$$

The estimates are noisy and vary depending on the strength of the signal (speckle). To get smooth estimate of f, the estimates $$\hat{f}_i(m) = \frac{1}{N}\sum_{n=1}^{N} \hat{f}_i(m, n)$$

are first averaged and then f(m) is found as a nth-order (e.g., $2^{nd}$ $3^{rd}$, etc.) polynomial is obtained via least squared error fitting.

Figure 4:
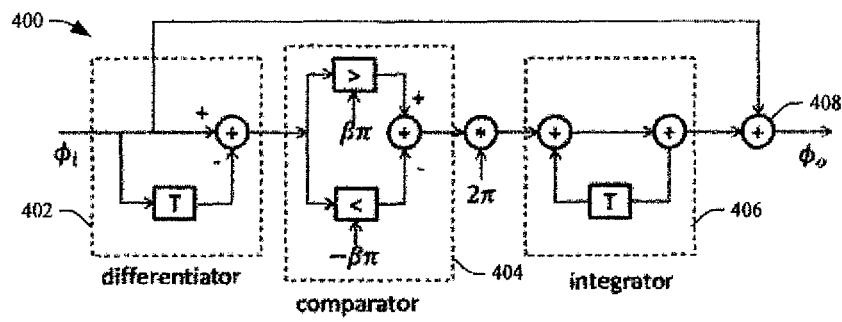
FIG. 4 schematically illustrates a phase unwrapper of the motion estimator.

FIG. 4 shows an example of a phase unwrapping approach. In FIG. 4, the phase unwrapping is achieved via a phase unwrapper 400. The phase unwrapper 400 receives, as an input, an input matrix $\Phi_I$ and outputs a matrix $\Phi_O$. In this example, the processing is done per column. However, other approaches (e.g., by row, element, the entire matrix, etc.) are also contemplated herein. A differentiator 402 differentiates the input phase $\varphi_i(m, n)$: $\Delta\varphi(m, n)=\varphi_i(m, n)-\varphi_i(m-1, n)$. A comparator 404 compares the result a predetermined threshold to determine aliasing. In one instance, the threshold is $\pm\beta\pi$, where $\beta$ is a constant less or equal to 1 ($\beta\leq1$). The output of the comparator 404 indicates aliasing. Every time aliasing occurs, a $\pm2\pi$ value must be added to the phase, depending on a sign of the difference. An integrator 406 integrates the adjustment value. An adder 408 adds the integrated value and the input phase.

Returning to FIG. 3, a motion estimator 306 estimates a motion $u_l(m, n)$ (where l is an iteration index from 0 to s such as 1, 2, 3, 5, 17, 100, etc.) based on $x_{ic}(m, n)$ and $x_{jc}(m, n)$ using a phase-shift estimation and converting from phase to motion via the mean frequency estimation f(m). As described in greater detail below, in one instance, an initial (l=0) motion estimation $n_0(m, n)$ uses a cross-cross correlation at lags (0,0), 0 samples and 0 lines offset, and, for each iteration (l=1, 2, 3 etc.), the motion estimator 306 finds a phase shift between the two frames at lags $k_l$m, n) and estimates a new motion estimate $u_l(m, n)$ using this phase shift, producing a more refined or accurate motion estimate $u_l(m, n)$. The cross-correlation estimates are complex-valued, and the angle (phase) of the cross correlation function corresponds to the motion.

A surface fitter 308 fits a surface to the motion estimate $u_l(m, n)$, which reduces variations and removes outliers and thus noisy motion estimates, or smooths the motion estimate. In one instance, the surface is fitted using least mean squares 2D polynomial fitting, where the polynomial coefficients are: P=G$u_l$, where G is a matrix derived from solving a least-squares fit for a $3^{rd}$ order surface. Other orders (e.g., nth order) of the polynomial maybe used, depending on the tradeoff between precision and computational requirement. Here, $u_l$ is the matrix with the estimates of the motion. The surface can be found as $u_{fit}(m, n)=P(0)+P(1)n+P(2)m+P(3)n^2+P(4)mn+P(5)m^2+P(6)n^3+P(7)n^2m+P(8)nm^2+P(9)m^3$.

The surface fitter 210 may also identify a smooth edge between the different lags, which facilitates the phase-unwrapping discussed below.

A quantizer 310 quantizes the fitted motion estimate and find lags k(m, n) at which the cross-correlation between the two frames will give a more precise estimate than $u_l(m, n)$. By way of example, the fitted surface can be quantized to give the lags where to calculate the cross correlation at next iteration:

$$k(m, n) = \text{round}\left(\frac{2f_s}{c}u_{fit}(m, n)\right).$$

A decision component 212 receives, as an input, the current lags and the new lags and determines whether the motion estimate will be refined through an iteration or a final motion estimate $u_l(m, n)$ will be output based on various stopping criteria. Such criteria may include, but is not limited to, a predetermined number of iterations (e.g., l=1, or one iteration and two motion estimates), a predetermined difference between the current and new lags, a predetermined time interval, on demand based on a user input, and/or other stopping criteria.

Figure 5:
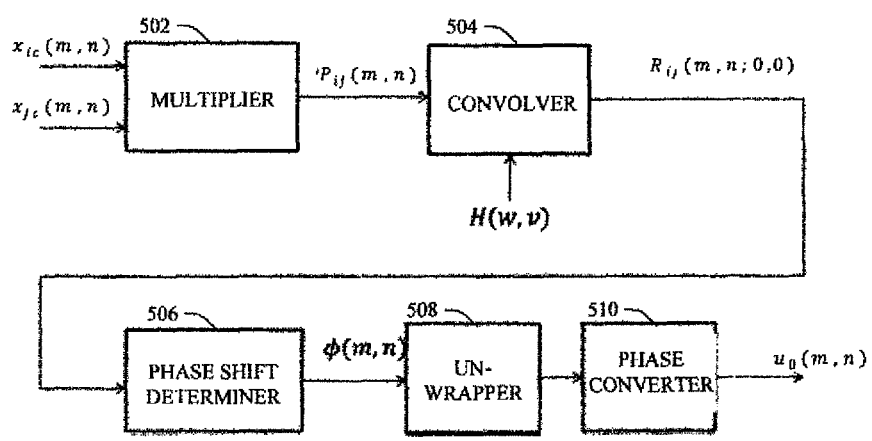
FIG. 5 schematically illustrates an example of the motion estimator for an initial motion estimate.
Figure 6:
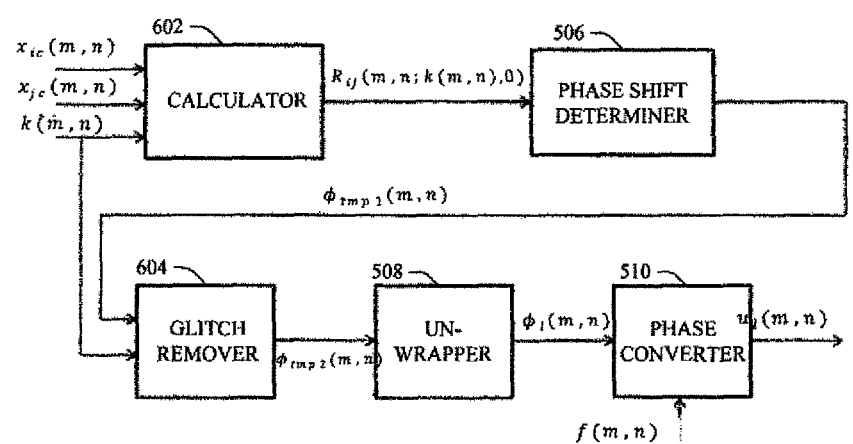
FIG. 6 schematically illustrates an example of the motion estimator for a subsequent iteration motion estimate(s).

As briefly discussed above, the motion estimator 306 estimates the motion $u_l(m, n)$. FIG. 5 shows example components for estimating an initial motion estimate at iteration l=0, and FIG. 6 shows example components for estimating a subsequent motion estimate(s) at l=1, . . . s.

With FIG. 5, the estimation of the motion is based on the lag-0 cross correlation between the two frames:

$$R_{ij}(m, n; 0, 0) = \sum_{v=-\frac{V}{2}}^{\frac{V}{2}} \sum_{w=-\frac{W}{2}}^{\frac{W}{2}} H(v, w) \times x_{ic}(m+v, n+w) \times x_{jc}^*(m+v, n+w).$$

A multiplier 502 multiplies the two input matrices $x_{ic}(m, n)$ and $x_{jc}(m, n)$, element by element, producing $P_{ij}(m, n)$. A convolver 504 convolves $P_{ij}(m, n)$ with an averaging window H(v, w). If the averaging window H(v, w) is a 2D rectangular function, then the convolution is reduced to four (4) additions and two (2) subtractions per sample recursive implementation of a running average. A phase shift determiner 506 determines a phase shift at pixel (m, n) as $$\phi(m, n) = \arctan\frac{R_{iji}(m, n; 1, 0)}{R_{ijr}(m, n; 1, 0)}.$$

An unwrapper 508 unwraps the phase using the above approach wherein $\Phi$=unwrap($\Phi$) and/or other approach. A phase converter 510 converts the phase to the initial motion estimate as $$u_0(m, n) = \frac{c}{4\pi f(m)}\phi(m, n).$$

Turning to FIG. 6, the estimation of the motion at iteration l=1, . . . s is similar to that for the initial motion estimate except that the cross correlation is performed at lags k(m, n), or $$R_{ij}(m, n; k(m, n), 0) =$$

$$\sum_{v=-\frac{V}{2}}^{\frac{V}{2}} \sum_{w=-\frac{W}{2}}^{\frac{W}{2}} H(v, w) \times x_{jc}(m+v, n+w) \times x_{ic}^*(m+v+k(m,n), n+w).$$

In FIG. 6, a calculator 602 includes the multiplier 502 and the convolver 504, which are not visible in this example. The multiplier 502 multiplies the two input matrices $x_{ic}(m, n)$ and $x_{jc}(m, n)$, based on the lags k(m, n), element by element. For this, minimum and maximum values of k(m, n) are determined. The multiplier 502 iterates from min(k(m, n)) to max(k(m, n)). For every lag κ every element $x_{ic}$ is multiplied by the complex conjugate of element of $x_{jc}$, taken at the respective lag κ. The convolver 504 convolves the output matrix P with the filter H(w, v), and the elements at positions (m, n) in $R_{ij}$, for which k(m, n)=κ are updated.

Once the cross correlation is found, the phase shift determiner 506 determines a phase of each cross correlation as:

$$\phi_{tmp1}(m, n) = \arctan \frac{R_{iji}(m, n; 1, 0)}{R_{ijr}(m, n; 1, 0)}.$$

A glitch remover 604 removes the glitches by detecting and removing transitions in the matrix with lags K whose elements are k(m, n): $\Phi_{tmp2}$=unwrap_with_lags($\Phi_{tmp1}$, K). Note that at borders, where transitions occur in k(m, n), there are steps in the phase estimation which are not due to aliasing and are not caught by the unwrapping algorithm. The phase unwrapper 508 unwraps the phase using the unwrapping approach described herein and/or other approach. When the transition in lags is at the wrong pixel, a phase wrapping occurs although the lags are the same. As such, the unwrapping algorithm discussed herein can be applied: $\Phi_1$=unwrap($\Phi_{tmp2}$). The phase to distance converter 510 determines the motion as $$u_i(m, n) = \frac{c}{4\pi f(m)} \phi_i(m, n).$$

Figure 7:
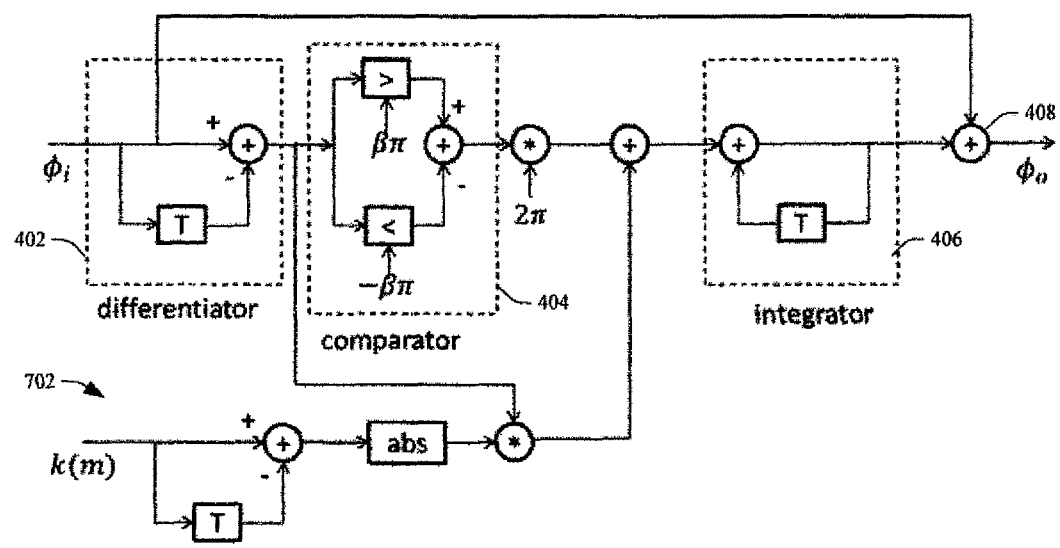
FIG. 7 schematically illustrates an example phase unwrapper with glitch removal for the subsequent iteration motion estimate(s).
Figure 8:
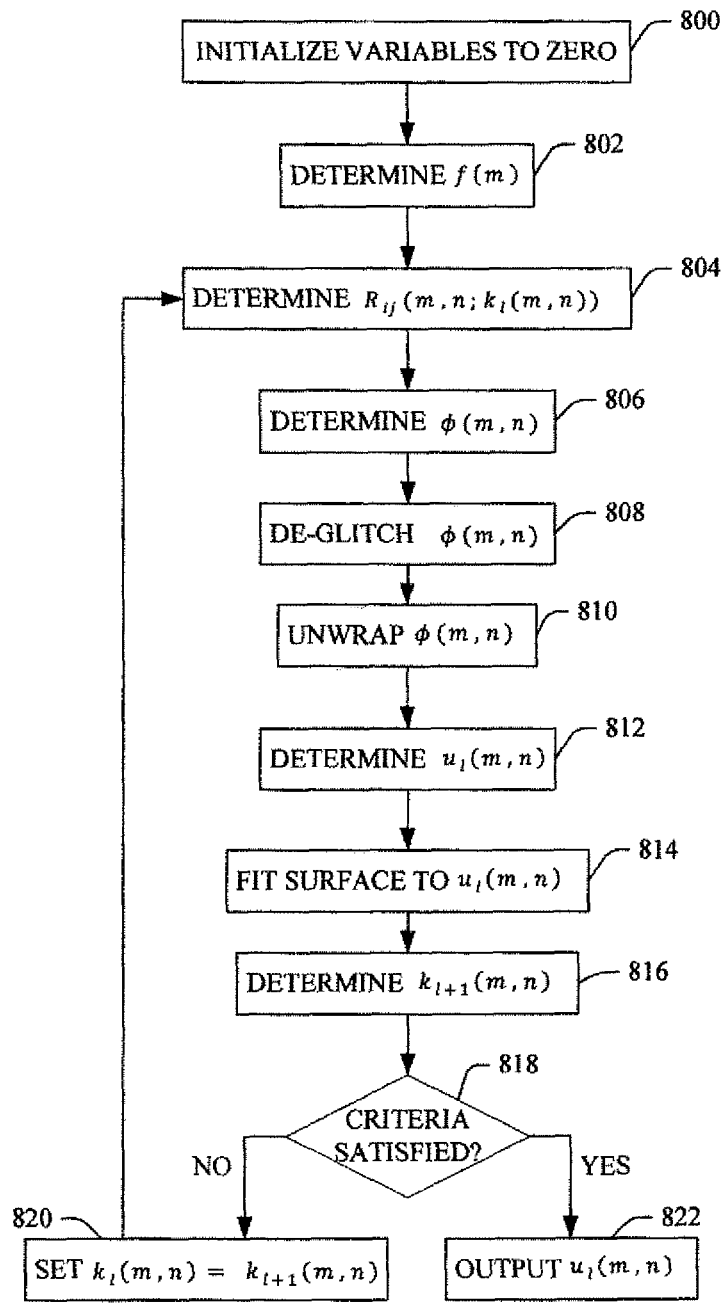
FIG. 8 schematically illustrates an example method for determining motion estimates via an iterative approach.

FIG. 7 show an example of a suitable phase unwrapping with glitch removal approach. FIG. 7 is similar to FIG. 4 with the inclusion of the lags as shown at 702. The phase unwrapping with lags operates upon data that is acquired along the same line. The line index is omitted for brevity. The inputs are the estimated phase $\Phi_i(m)$ and the lags k(m) at which the phase was estimated. As shown, both the lags and the phase are differentiated. The lags are integers and the information that is needed is the magnitude of the change. If such a change is detected, then this step is equal to the phase jump at that transition. The main path detects phase wrapping by comparing the phase difference to a threshold. The result is a series of pulses indicating the positions where the phase wraps and the magnitude of the phase wrapping. These series of impulses are integrated to generate a staircase like phase compensation function, which is added to the input phase FIG. 8 illustrates a method for estimating motion in connection with elastography imaging.

Note that the ordering of the following acts is for explanatory purposes and is not limiting. As such, one or more of the acts can be performed in a different order, including, but not limited to, concurrently. Furthermore, one or more of the acts may be omitted and/or one or more other acts may be added.

Generally, the initial motion estimate (l=0) is a particular case of the subsequent motion estimates (l>0) with all lags k(m, n) set to zero (0). The data for the initial and subsequent motion estimates can be processed by a same or different module.

At 800, k(m, n), $R_{ij}$(m, n), φ(m, n), $u_l$(m, n), and l are initialized to zero (0).

At 802, f(m) is determined as described herein.

At 804, $R_{ij}$(m, n; $k_l$(m, n)) is determined as described herein.

At 806, φ(m, n) is determined as described herein.

At 808, φ(m, n) is de-glitched as described herein

At 810, φ(m, n) is unwrapped as described herein.

At 812, $u_l$(m, n) is determined as described herein.

At 814, the surface $u_{fit}$(m, n) is fit to $u_l$(m, n).

At 816, new lags $k_{l+1}$(m, n) are determined as described herein.

At 818, stopping criteria is checked. In this example, the stopping criteria is based on an absolute difference between the lags $k_l$(m, n) and the new lags $k_{l+1}$(m, n), as described herein.

At 820, if the stopping criteria is not satisfied, k(m, n) is set to the new lag $k_{l+1}$(m, n), acts 804-816 are repeated.

At 822, if the stopping criteria is satisfied, $u_l$(m, n) is output as the final motion estimate. The final motion estimate can be used to generate elastography and/or other images.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An ultrasound imaging console, comprising:
   a beamformer that beamforms ultrasound echoes from an ultrasound transducer array of an ultrasound imaging system to produce at least a pair of consecutive frames of sets of scan lines;
   a pre-processor that pre-processes each of the frames to produce a pair of pre-processed frames, including a first frame and a second subsequent frame;
   a processor that:
     compresses an envelope of each of the first and second frames;
     estimates a mean frequency of the compressed first frame,
     calculates a cross correlation between the pair of compressed frames at a set of lags;
     determines a phase of the cross correlation;
     removes glitches in the phase;
     unwraps the de-glitched phase;
     converts the unwrapped phase to a motion estimate using the mean frequency;
     fits a surface to the motion estimate;

quantizes the fitted motion estimate to determine a subsequent set of lags;

generates an elastography image with the motion estimate in response to a difference between the set of lags and the subsequent set of lags satisfying predetermined difference criteria; and visually presents the elastography image.

2. The console of claim 1, wherein the processor initializes the set of lags to zero prior to calculating the cross correlation for an initial motion estimate.

3. The console of claim 2, wherein the processor generates a subsequent motion estimate in response to the difference between the set of lags and the subsequent set of lags failing to satisfy the predetermined difference criteria.

4. The console of claim 1, wherein the processor:

multiplies, element-by-element, elements in the pair of pre-processed frames, producing a first product matrix; and convolves the first product matrix with a predetermined transform to calculate the cross-correlation.

5. The motion processor of claim 4, wherein the pre-processing includes the processor applying a filter to the set of scan lines, applying the transform to the filtered sets of scan lines to create complex signals, frequency shifting the complex signals towards baseband, and decimating the frequency shifted signals to produce the pair of pre-processed frames.

6. The console of claim 5, wherein the transform is one of a Hilbert transform or a 2D rectangular function.

7. The console of claim 1, wherein the processor fits the surface with a 2D polynomial.

8. The console of claim 1, wherein the fitting of the surface at least one of smooths the motion estimate or removes false variations and noise.

9. The console of claim 1, where the subsequent set of lags includes non-zero cross-correlation lags.

10. The console of claim 9, wherein the processor generates a subsequent motion estimate using the non-zero cross-correlation lags.

11. The console of claim 1, further, comprising:

receive circuitry that receives the ultrasound echoes from the ultrasound transducer array.

12. The console of claim 11, further comprising:

transmit circuitry that actuates transducer elements of the transducer array to transmit ultrasound signals, wherein the ultrasound echoes are produced in response to the ultrasound signals interacting with structure.

13. A method, comprising:

pre-processing each frame of a pair of consecutive frames of beamformed ultrasound echoes from an ultrasound transducer array to produce a pair of pre-processed frames, including a first frame and a second subsequent frame;

iteratively estimating, via a processor, tissue motion between the first and second frames over at least one iteration by:

compressing an envelope of each of the first and second frames;

estimating a mean frequency of the compressed first frame, calculating a cross correlation between the pair of compressed frames at a set of lags;

determining a phase of the cross correlation;

removing glitches in the phase;

unwrapping the de-glitched phase;

converting the unwrapped phase to a motion estimate using the mean frequency;

fitting a surface to the motion estimate;

quantizing the fitted motion estimate to determine a subsequent set of lags;

generating an elastography image with the motion estimate in response to a difference between the set of lags and the subsequent set of lags satisfying predetermined difference criteria; and displaying the elastography image.

14. The method of claim 13, wherein the set of lags equals to zero.

15. The method of claim 13, wherein the subsequent set of lags are non-zero.

16. The method of claim 13, further comprising:

multiplying, element-by-element, elements in the pair of pre-processed frames to produce a first product matrix; and convolving the first product matrix with a predetermined transform to calculate the cross-correlation.

17. The method of claim 13, wherein removing glitches includes: detecting and removing transitions with predetermined lags.

18. The method of claim 13, wherein removing glitches from and unwrapping phase are performed concurrently by:

differentiating the phase and the set of lags;

comparing the differentiated phase to a predetermined threshold, producing a series of pulses indicating positions;

integrating the series of pulses to generate a phase compensation function; and adding the phase compensation function to the phase.

19. The method of claim 13, wherein de-glitched phase is unwrapped by:

differentiating the phase;

comparing the differentiated phase to a predetermined threshold $\pm\beta\pi$ to determine aliasing, where $\beta$ is a constant less or equal to one;

adding $\pm 2\pi$ to the differentiated phase every time aliasing occurs;

integrating the differentiated phase; and adding a result of the integrating to the phase.

20. A non-transitory computer readable storage medium encoded with computer executable instructions, which, when executed by a processor, causes the processor to:

compresses an envelope of each of first and second frames, which are frames of a pair of pre-processed consecutive frames of beamformed ultrasound echoes from an ultrasound transducer array;

estimate a mean frequency of the compressed first frame, calculate a cross correlation between the pair of compressed frames at a set of lags;

determine a phase of the cross correlation;

remove glitches in the phase;

unwrap the de-glitched phase;

convert the unwrapped phase to a motion estimate using the mean frequency;

fit a surface to the motion estimate;

quantize the fitted motion estimate to determine a subsequent set of lags;

generate an elastography image with the motion estimate in response to a difference between the set of lags and the subsequent set of lags satisfying predetermined difference criteria; and display the elastography image.

* * * * *